United States Patent [19]

Craig et al.

[11] 4,205,233
[45] May 27, 1980

[54] AUTOMATIC BUCKY LOCK

[75] Inventors: James R. Craig, Glenview; George W. Otto, Jr., Elmhurst, both of Ill.

[73] Assignee: Raytheon Company, Lexington, Mass.

[21] Appl. No.: 963,064

[22] Filed: Nov. 22, 1978

[51] Int. Cl.² .......................................... G01N 21/00
[52] U.S. Cl. ................................ 250/439 R; 250/452
[58] Field of Search .................. 250/439 R, 452, 508, 250/509, 468, 402, 401

[56] References Cited

U.S. PATENT DOCUMENTS

| | | | |
|---|---|---|---|
| 1,957,720 | 5/1934 | Nelson | 250/452 |
| 2,123,528 | 7/1938 | Goldfield | 250/452 |
| 2,536,212 | 1/1951 | Ostroff | 250/452 |

Primary Examiner—Craig E. Church
Attorney, Agent, or Firm—Richard M. Sharkansky; Joseph D. Pannone; Milton D. Bartlett

[57] ABSTRACT

An X-ray radiographic or fluoroscopic table which includes as a part thereof a bucky including a frame containing a removable cassette-supporting tray, the bucky being movable in the long direction of the table and having a front opening for slidably receiving the tray, the bucky further carrying switch means operable in conjunction with switch-operating means on the tray, the switch being operable, when the tray is located in either cassette-loading or in filming position, to activate means for rendering the bucky immovable, which means is inactivated to allow the bucky to be adjusted when the tray is located at a midpoint between those positions.

18 Claims, 8 Drawing Figures

AUTOMATIC BUCKY LOCK

BACKGROUND OF THE INVENTION

This invention relates to X-ray fluoroscopic tables and the like and has particular reference to such tables which are adapted to support a patient in position so that X-rays or other similar radiation may be directed through the patient to an image receptor which comprises a radiation-sensitive film for producing a visible image of the irradiated area of the patient.

In conventional X-ray systems the X-ray sensitive receptor or film is suitably mounted in a cassette which is supported on a tray, called a bucky tray, adapted to be slid into and out of a support called a bucky frame. The bucky frame is a conventional shallow boxlike device having an open top and a front opening through which the tray is inserted into the frame whereby X-rays entering the frame through the open top will impinge upon the film supported on the tray. The table has an X-ray transparent top upon which the patient reposes, and the bucky frame is located in the table beneath the top. Since it is undesirable to continually reposition a patient during a series of X-ray exposures, the bucky frame is movably mounted in the table so that it may be adjusted with respect to the patient in a direction longitudinally of the table.

The bucky (frame and tray) weighs over twenty pounds, and the cassette varies from one to eight pounds and may be as large as seventeen inches square. Therefore, considerable weight is involved when a bucky frame, tray and cassette are to be moved as a unit.

Movement of the bucky frame, and consequent adjustment of the position of the film, has been accomplished by attaching the ends of a cable to the frame and mounting the cable on pulleys so that, upon manual manipulation of a crank attached to one of the pulleys, the pulleys can be rotated with consequent movement of the cable and frame.

In a tilting table the bucky frame is counterbalanced so that the operator can position it easily regardless of the tilt position of the table. However, the counterweight can accomodate only one combination of cassette and bucky weights. Therefore, it was necessary to additionally provide a mechanical lock to immobilize the bucky in its adjusted position.

Other prior developments included the provision of a rack and pinion device for moving the bucky and a mechanical clamp for locking it in place. A still later development involved the use of an electric motor with push button operation to move the cable and an electromagnet for rendering a pulley immovable to lock the bucky in adjusted position.

To install a cassette, the operator will pull a tray out of a bucky frame to its maximum "out" position as determined by a mechanical retainer, place the cassette between two clamping bars, and manipulate a lever which sets the bars. The tray is then reinserted in the bucky frame. Since both hands are required to install the cassette, it is a cumbersome and awkward maneuver by the operator to activate and deactivate a separate bucky lock during the loading and unloading procedures. When an operator neglects to operate the lock the bucky may inadvertently move with consequent damage to the mechanism or disturbance of the patient.

SUMMARY OF THE INVENTION

The above and other objections to the prior art are overcome in the present invention by the provision of an adjustable bucky with means for automatically locking the bucky when the tray is in loading or exposure position and for automatically unlocking the bucky and permitting it to be moved when the tray is in an intermediate position.

The bucky frame is movable longitudinally of the table by means of a cable and metal pulleys, with a balance weight being located on the cable for counterbalancing the weight of the bucky frame-tray assembly. The base of the frame carries a switch, such as a magnetically actuated reed switch or axial travel switch which is electrically connected to an electromagnet located in close proximity to one of the metal pulleys. The switch is adapted to be actuated by a magnet which is carried by the tray whereby when the tray is slid into the frame to an intermediate position the magnet will cause the switch to open the electrical circuit to the electromagnet, freeing the pulley, and allowing the bucky frame and tray assembly to be moved.

When the tray is pulled out to load position where a cassette may be positioned on or clamped to the tray, or is pushed in to the home position where an X-ray exposure may be made, the magnet is not located close enough to the switch to cause the switch to be activated. Thus, the switch, which is normally closed, will complete the circuit to the electromagnet, causing the adjacent pulley, and consequently the bucky assembly, to be immobilized.

With a table and bucky assembly structured in accordance with this invention, an operator can use both hands to locate a cassette on a tray held by an immobilized bucky frame, and then by inserting the tray to an intermediate point in the frame he can simply adjust the bucky to a position where the tray is properly aligned in a preselected position, following which he can then push the tray the remainder of the way into the frame to immobilize it and permit an X-ray exposure to be made.

BRIEF DESCRIPTION OF THE DRAWINGS

The above and other advantages of the invention will become apparent from the following description taken in connection with the accompanying drawings, wherein.

DESCRIPTION OF THE PREFERRED EMBODIMENTS

Figure 1:
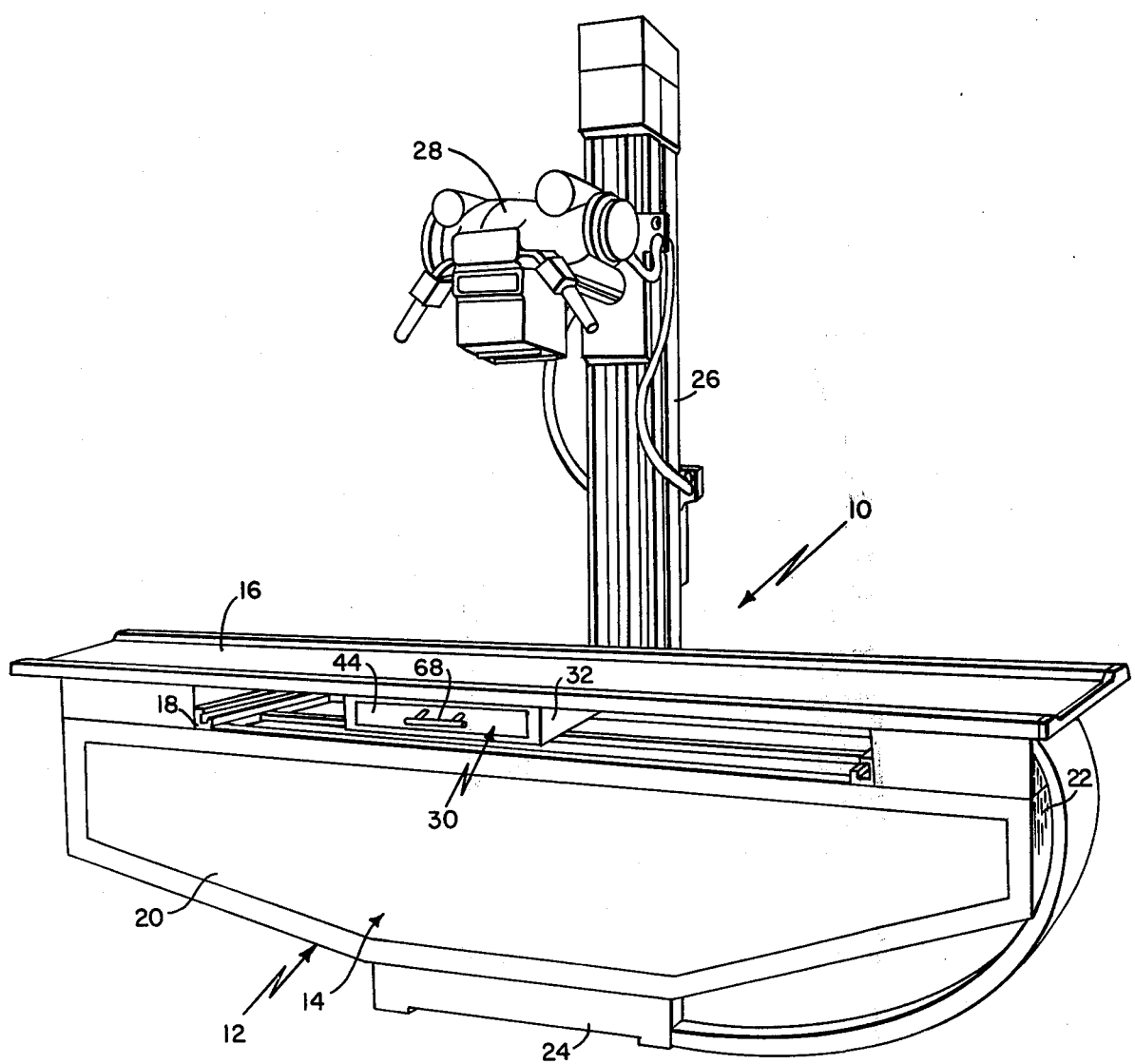
FIG. 1 is a perspective view of a fluoroscopic X-ray table embodying the invention.

Referring more particularly to the drawings, wherein like characters of reference designate like parts throughout the several views, there is shown in FIG. 1 and X-ray apparatus 10 which is supported by an X-ray table 12 having a base 14 and a top 16. The top 16 is suitably secured upon a frame or carriage 18 for planar movement in any direction, the means for accomplishing such movement not comprising a part of this invention. The base 14 has a depending front panel 20 and end panels 22 which overlie a fixed pedestal 24 upon which the base is tiltable as is well known in the art.

Although not a part of the present invention, the X-ray apparatus 10 is shown briefly as including a tube stand 26 that supports a vertically adjustable X-ray generator 28 which is normally positioned above the table top 16. Details of the generator and associated mechanism are well known and, therefore, not described herein.

Between the top of the base 14 and the table top 16 is a longitudinally extending space which opens at the front of the table so that a bucky 30 may be inserted and adjusted beneath the top 16 so as to be properly positioned with respect to the X-ray generator 28. Thus, when the generator 28 and the bucky 30 are properly related, X-rays from the generator 28 will pass through a patient lying on top 16 and through the top to a film which is carried within the bucky.

Figure 2:
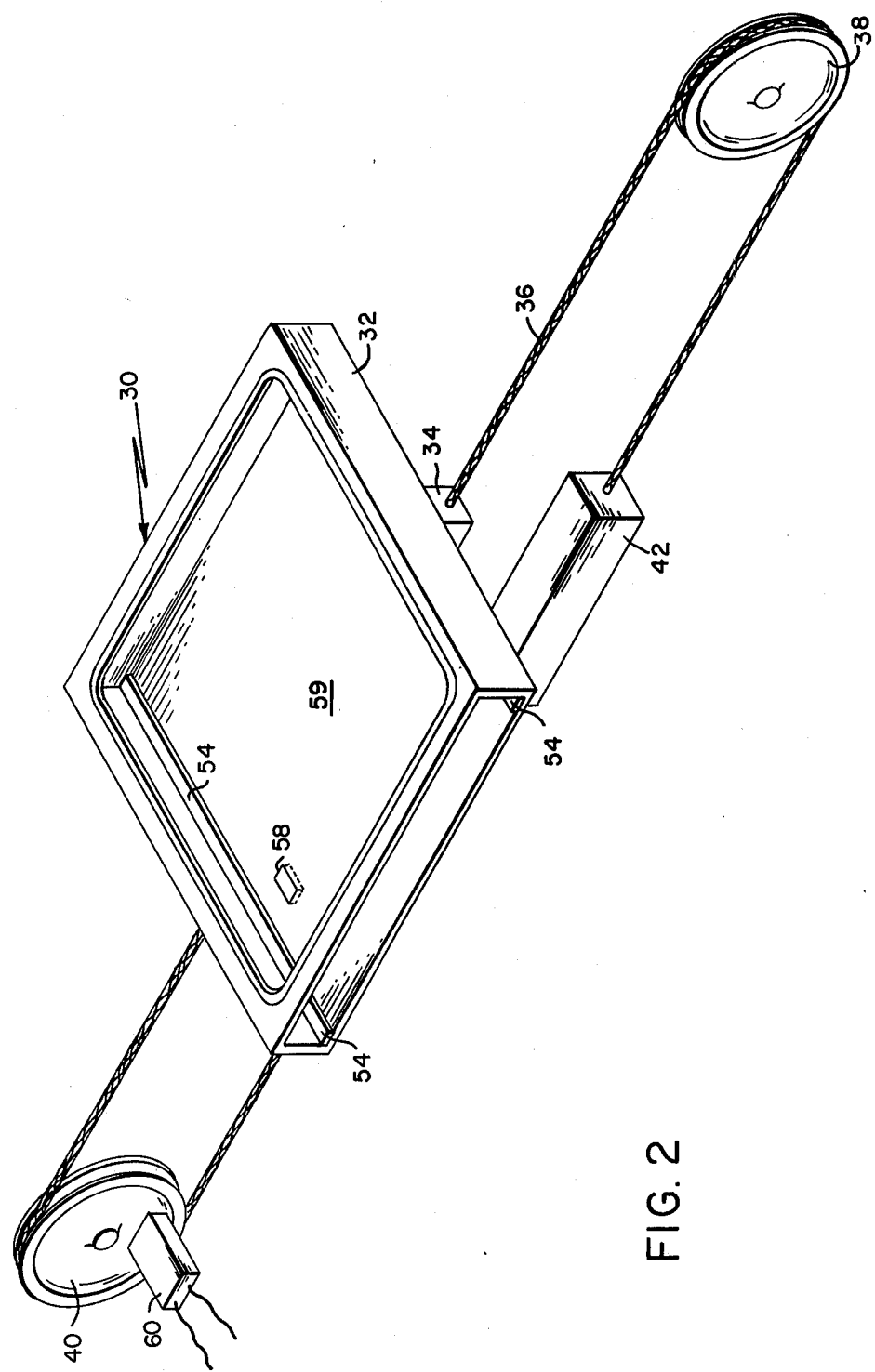
FIG. 2 is an isometric view pictorially illustrating the bucky adjusting system.
Figure 3:
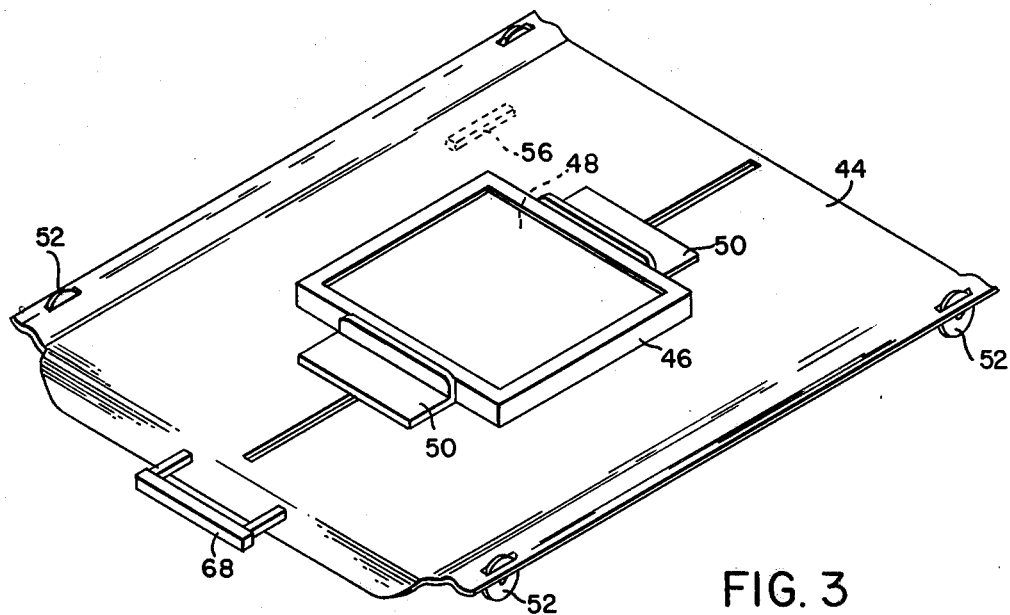
FIG. 3 is an isometric view of a bucky tray embodying the invention.

The bucky 30 includes a bucky frame 32 of which is shown in FIG. 2. The frame 32 carries a fixed clamp or block 34 on its under side to opposite sides of which are attached the respective opposite ends of a cable 36. Cable 36 is extended over spaced pulleys 38 and 40 as shown in FIG. 2, which pulleys are conveniently rotatably mounted in respective end portions of the table base 14. Thus, the bucky frame 30 may be easily slid longitudinally of the table within the space beneath the top 16. A weight 42 is carried by the cable 36, as shown in FIG. 2, to counterbalance the weight of the bucky frame 30 and a bucky tray and cassette carried by the frame.

The bucky frame 30 is open at the top and has a front opening through which a bucky tray 44 may be inserted into the frame. The tray 44 supports a cassette 46 which carries an X-ray sensitive film 48. Cassette 46 is centered on the tray 44 between adjustable clamps 50 and is adapted to be aligned with the X-ray generator 28 in the known conventional manner.

The sides of the tray 44 are provided with suitable rollers 52 which ride along suitable track portions 54 of the frame 32 when the tray is being inserted into or withdrawn from the frame. In accordance with this invention, the under side of the tray 44 has attached to it near one side a magnet 56, preferably a bar magnet, which is adapted to be positioned in proximity to a switch 58 carried by the bottom 59 of the frame 32 when the tray is withdrawn to a midpoint out of the frame. When the tray 44 is located in the position illustrated in FIG. 6, the magnet 56 will be located immediately above the switch 58.

Figure 8:
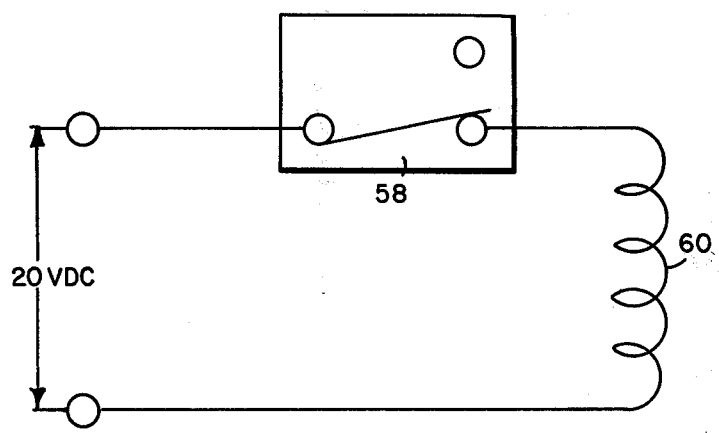
FIG. 8 is a schematic diagram of the bucky locking circuit.
Figure 4:
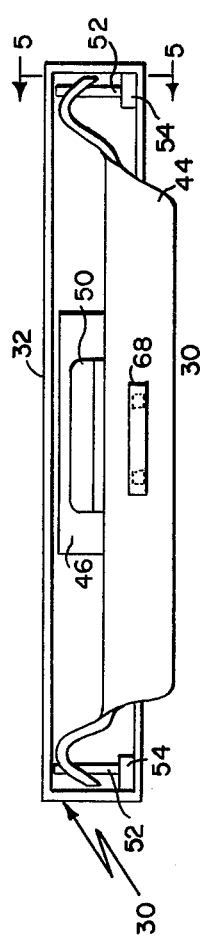
FIG. 4 is a front elevational view of a bucky including frame and tray.

Switch 58, which may be a reed switch or an axial travel switch, for example, is preferably a normally closed single pole double throw switch connected at one side to a suitable source of power SC (see FIG. 8) such as 20 or 24 volts DC and at the opposite side to an electromagnet 60 which is located closely adjacent the face of one of the pulleys 40. Since the switch 58 is normally closed, the electromagnet 60 will normally be energized. This will immobilize the pulley 40 and consequently the cable 36 and bucky 30 can not be normally moved.

Figure 7:
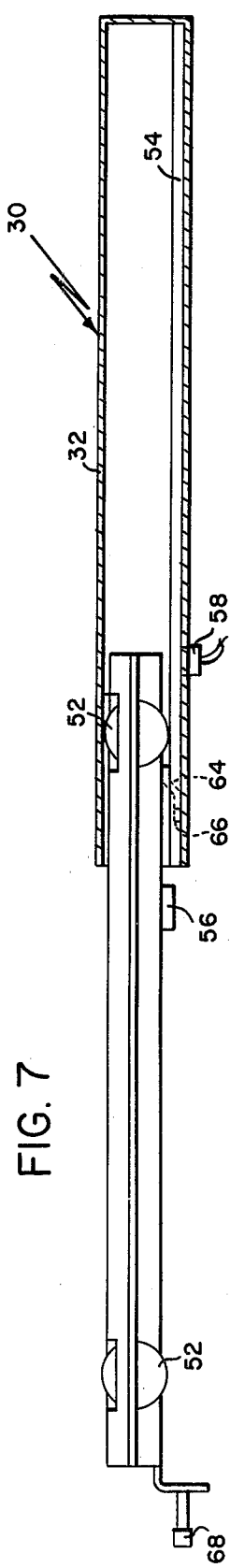

When a cassette 46 is to be loaded onto a tray 44, the tray is pulled out of the bucky frame 32 to the fullest extent possible without removing it entirely, this being controlled by a spring member 64 (FIG. 7) which is fixed to the under side of the tray 44 in a position where it will engage a stop 66 on the bucky frame 32. Thus, when the tray is pulled out of the frame to the point where the spring member 64 engages the stop 66, as shown in FIG. 7, the magnet 56 is sufficiently far enough away from the switch 58 that its magnetic field will not cause the switch to open. Thus, the bucky is immobilized and the operator may use both hands to load a cassette 46 on the tray 44.

Figure 6:
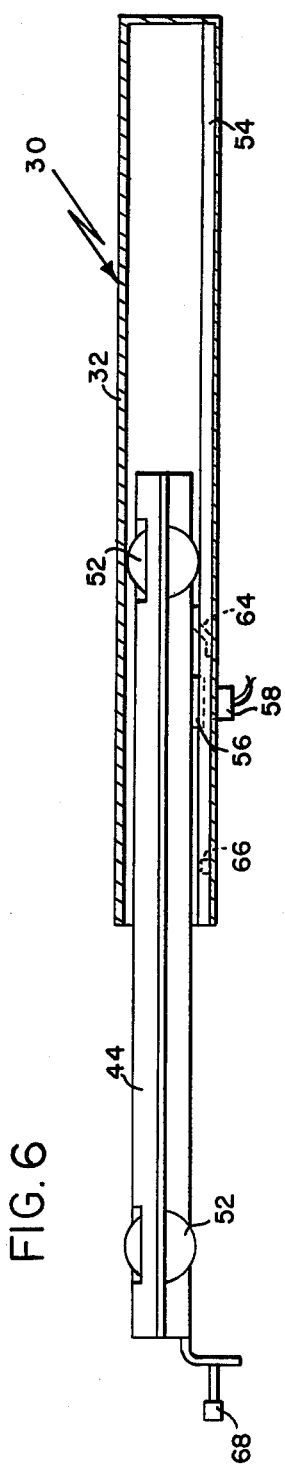

When the tray 44 is pushed into the frame 32 to approximately the midpoint, as shown in FIG. 6, the magnet 56 will open switch 58, deenergizing the electromagnet 60, and allowing the bucky 30 to be adjusted longitudinally of the table. This can be done by the operator very easily by merely grasping the handle 68 on the tray and applying pressure in the direction in which the bucky is to be moved.

Figure 5:
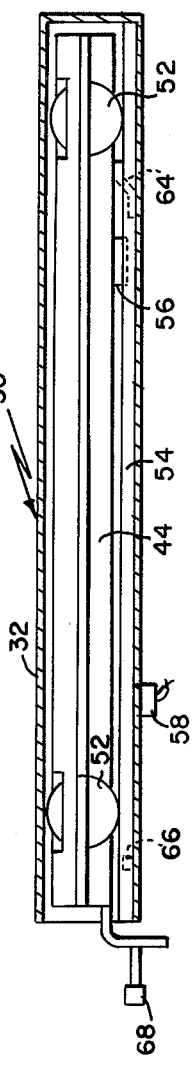
FIGS. 5, 6 and 7 are sectional views taken on line S—S of FIG. 4 showing the bucky tray in three different positions in the bucky frame.

When the bucky 30 has been suitably adjusted, the tray 44 then will be pushed all the way in to "home" position as shown in FIG. 5. When in home position an X-ray exposure may be taken and, therefore, it is important that the bucky be stationary. To permit this the magnet 56 is remote from the switch 58. Thus, the switch is in its normally closed condition and the electromagnet 60 is energized to immobilize the bucky.

From the foregoing it will be apparent that all of the objectives of this invention have been achieved by the novel features shown and described. It will also be apparent that various modifications and changes in the features shown and described may be made by those skilled in the art without departing from the spirit of the invention as expressed in the accompanying claims. Therefore, all matter shown and described is to be interpreted as illustrative and not in a limiting sense.

What is claimed is:

1. A fluoroscopic table comprising a base, a top position on said base, a bucky positioned beneath said top, operating means for moving said bucky beneath the top and longitudinally thereof, said bucky comprising a boxlike frame having a front opening and a tray slidable into and out of the frame through said opening, and means responsive to selective positioning of said tray within the frame for immobilizing said bucky selected positions of said tray within the frame.

2. A table as set forth in claim 1 wherein said tray is positionable within the frame at a first station wherein a film cassette may be loaded thereon, a second station wherein an X-ray exposure may be made, and a third stage, and said immobilizing means is operable when the tray is positioned at said first or second station.

3. A table as set forth in claim 2 wherein said immobilizing means is inoperable when the tray is positioned at said third station.

4. A table as set forth in claim 1 wherein said immobilizing means comprises an electrically operated lock on said operating means, and electrical switch means located on said bucky and electrically connected to said lock.

5. A table as set forth in claim 4 wherein said bucky frame and said bucky tray each includes an effective switching area, and said areas are relatively movable into and out of switching proximity upon adjustment of the tray within the frame.

6. A table as set forth in claim 5 wherein one of said switching areas carries a switch device and the other switching area carries a switch-actuating device, said devices being relatively movable into switch-operating proximity when the tray is positioned at a selected station in said frame.

7. A table as set forth in claim 4 wherein said lock is an electromagnet.

8. A table as set forth in claim 7 wherein said frame carries a magnetically operable switch electrically connected to said electromagnet, and said tray carries a magnet which is positioned in operating proximity to the switch when the tray is positioned at a selected station within the frame.

9. A table as set forth in claim 8 wherein said magnet is positioned in operating proximity to the switch when the tray is located at said third station.

10. A fluoroscopic table comprising a base, a top positioned on said base, a bucky positioned beneath said top operating means for moving said bucky beneath the top and longitudinally thereof, said operating means comprising a first pulley of magnetically attractable material and a second pulley, said pulleys being rotatably mounted in respective end portions of said one of said base, and a cable wound over said pulleys and having its ends attached to said bucky comprising a boxlike frame having a front opening and a tray slidable into and out of the frame through said opening, and means responsive to selective positioning of said tray within the frame for immobilizing said bucky.

11. A table as set forth in claim 10 wherein said tray is positionable within the frame at a first station wherein a film cassette may be loaded thereon, a second station wherein an X-ray exposure may be made, and a third stage, and said immobilizing means is operable when the tray is positioned at said first or second station.

12. A table as set forth in claim 1 wherein said immobilizing means is inoperable when the tray is positioned at said third station.

13. A table as set forth in claim 10 wherein said immobilizing means comprises an electrically operated lock operatively associated with said operating means, and electrical switch means located on said bucky and electrically connected to said lock.

14. A table as set forth in claim 13 wherein said bucky frame and said bucky tray each includes an effective switching area, and said areas are relatively movable into and out of switching proximity upon adjustment of the tray within the frame.

15. A table as set forth in claim 14 wherein one of said switching areas carries a switch device and the other switching area carries a switch-actuating device, said devices being relatively movable into switch-operating proximity when the tray is positioned at a selected station in said frame.

16. A table as set forth in claim 13 wherein said lock is an electromagnet.

17. A table as set forth in claim 16 wherein said frame carries a magnetically operable switch electrically connected to said electromagnet, and said tray carries a magnet which is positioned in operating proximity to the switch when the tray is positioned at a selected station within the frame.

18. A table as set forth in claim 17 wherein said magnet is positioned in operating proximity to the switch when the tray is located at said third station.

* * * * *

UNITED STATES PATENT OFFICE
CERTIFICATE OF CORRECTION

Patent No. 4,205,233  Dated May 27, 1980

Inventor(s) James R. Craig and George W. Otto, Jr.

It is certified that error appears in the above-identified patent and that said Letters Patent are hereby corrected as shown below:

Column 4, line 37-38, change "position" to --positioned--;

Signed and Sealed this

Twenty-third Day of December 1980

[SEAL]

*Attest:*

SIDNEY A. DIAMOND

*Attesting Officer*  *Commissioner of Patents and Trademarks*